US008919555B2

(12) United States Patent
Choudhury et al.

(10) Patent No.: US 8,919,555 B2
(45) Date of Patent: Dec. 30, 2014

(54) MEDICAL SHARPS STORAGE DEVICE AND METHOD OF USING THE SAME

(71) Applicants: Sambhu N. Choudhury, Cincinnati, OH (US); Sean M. Lynch, Cincinnati, OH (US); Arturo David Sanchez, Lebanon, OH (US)

(72) Inventors: Sambhu N. Choudhury, Cincinnati, OH (US); Sean M. Lynch, Cincinnati, OH (US); Arturo David Sanchez, Lebanon, OH (US)

( * ) Notice: Subject to any disclaimer, the term of this patent is extended or adjusted under 35 U.S.C. 154(b) by 0 days.

(21) Appl. No.: 13/838,720

(22) Filed: Mar. 15, 2013

(65) Prior Publication Data

US 2014/0110290 A1    Apr. 24, 2014

Related U.S. Application Data

(63) Continuation-in-part of application No. 13/224,135, filed on Sep. 1, 2011.

(60) Provisional application No. 61/379,056, filed on Sep. 1, 2010.

(51) Int. Cl.
*B65D 83/10* (2006.01)
*A61M 5/32* (2006.01)

(52) U.S. Cl.
CPC ............... *A61M 5/3205* (2013.01); *A61M 5/32* (2013.01)
USPC .......................................... 206/370; 206/366

(58) Field of Classification Search
CPC ..................... B65D 83/0454; A61B 17/06161; A61B 17/06166; A61B 17/3217

USPC .......... 206/366, 370, 359, 438, 380, 539, 533
See application file for complete search history.

(56) References Cited

U.S. PATENT DOCUMENTS

| | | |
|---|---|---|
| 2,131,807 A | 10/1938 | Jerum |
| 3,727,658 A | 4/1973 | Eldridge, Jr. |
| 3,944,069 A | 3/1976 | Eldridge, Jr. |
| 4,008,802 A | 2/1977 | Freitag |
| 4,013,109 A | 3/1977 | Sandel |
| 4,026,066 A | 5/1977 | Reiner et al. |
| 4,167,230 A | 9/1979 | Barratt |
| 4,193,496 A | 3/1980 | Barratt |
| 4,383,615 A | 5/1983 | Aquino |
| 4,524,891 A | 6/1985 | Silva |
| 4,586,614 A | 5/1986 | Ger |
| 4,814,592 A | 3/1989 | Bradt et al. |
| 4,828,107 A | 5/1989 | Spencer |
| 4,943,939 A | 7/1990 | Hoover |

(Continued)

FOREIGN PATENT DOCUMENTS

WO            98/29322            7/1998

*Primary Examiner* — David Fidei
(74) *Attorney, Agent, or Firm* — Shoemaker and Mattare

(57) ABSTRACT

A needle storage device includes a base having a center post, and a tray disposed around the post. The tray has dividers defining multiple slots for receiving needles and other surgical instruments. A cover over the tray has an opening which exposes only one of those slots at a time. A needle other sharp device may be inserted through the opening into the slot below. The tray has a hub or button, exposed through a central opening in the cover, which can then be depressed and released to move the tray up and down between the base and the cover. A mechanism comprising teeth on both the tray and the cover angularly increments the tray beneath the opening, exposing a neighboring slot each time the tray is depressed.

6 Claims, 5 Drawing Sheets

(56) References Cited

U.S. PATENT DOCUMENTS

| | | |
|---|---|---|
| 5,150,788 A | 9/1992 | Weissman |
| 5,316,142 A | 5/1994 | Jain |
| 5,347,078 A | 9/1994 | Eckels |
| 5,487,600 A | 1/1996 | Griffin |
| 5,590,774 A | 1/1997 | Roberts |
| 5,595,296 A | 1/1997 | Wood |
| 5,799,788 A | 9/1998 | Webb |
| 5,873,462 A | 2/1999 | Nguyen et al. |
| 6,230,888 B1 | 5/2001 | Frieze et al. |
| 6,296,127 B1 | 10/2001 | Tseng |
| 489,822 A1 | 5/2004 | Koseki |
| 6,840,377 B2 | 1/2005 | Yu |
| 7,086,198 B2 | 8/2006 | Hayden |
| 7,134,550 B2 | 11/2006 | Groth |
| 2005/0205595 A1* | 9/2005 | Lepke et al. .......... 221/87 |

* cited by examiner

MEDICAL SHARPS STORAGE DEVICE AND METHOD OF USING THE SAME

This application is a continuation-in-part of copending application Ser. No. 13/224135, filed Sep. 1, 2011, and claims benefit provisional U.S. patent application Ser. No. 61/379,056, filed Sep. 1, 2010.

STATEMENT REGARDING FEDERALLY SPONSORED RESEARCH

Not applicable.

NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND ON THE INVENTION

1. Field of the Invention

The present invention relates generally to a device for receiving medical sharps such as, for example, needles, blades, and other sharp objects, and more to a device for receiving medical sharps that counts and stores medical sharps ergonomically and efficiently.

2. Description of the Related Art

Surgery is done with multiple small sharp items that could be lost in the body prior to closure and accidentally left in a position that allows sticking or cutting of the operative employees or the surgeon. Recording and storing medical sharps, e.g., needles, scalpels, blades, etc., are critical safety measures in the operating room. For example, these items are routinely accounted for prior to the closure of an operative wound. Thus, it is necessary that the device receiving and containing these items must be a safe receptacle that will prevent the loss of its contents. Further, the device must allow a user to safely position the items in the device to ensure all used sharp items are accounted for prior to the closure of the open wound.

Currently there are mechanisms that allow a user to position needles and sharp blades into a ridged and numbered receptacle or into a pincushion that is similarly numbered. However, if a needle is dull or broken, these needles cannot be easily locked into their appropriate receptacle position safely.

U.S. Pat. No. 3,944,069 to Eldridge discloses a "Receiver for Disposable Surgical Implements" which is provided with a pair of foldably connected pads, wherein each pad comprises a penetrable top layer and a penetration resisting bottom lamination. As each surgical implement is removed from the patient, it is inserted through the top layer and retained for eventual counting. The pads may then be folded together covering the sharp edges and then safely disposed of. However, various implements such as hypodermic needles, surgical needles, and small surgical knives can be inserted into available space of each pad. Thus, because various instruments may be inserted in a random fashion, the device does not provide a means for efficiently accounting for surgical instruments.

The devices in U.S. Pat. No. 4,013,109 to Sandel and Eldridge utilize magnetic force to retain surgical instruments made of ferrous metals. In particular, Sandel discloses a hinged container for magnetically retaining surgical needles. As surgical instruments are removed from the body, they are deposited within the hinged container and held in position there by a magnetic means that completely covers an interior portion. However, a shortcoming of these devices is that only ferrous materials can be retained by the magnetic surfaces. Further, there is a tendency for the ferrous materials to become magnetized to themselves and become attracted to one another.

U.S. Pat. No. 4,008,802 to Freitag discloses a pad of resilient material having consecutively numbered receiving zones, wherein needles are inserted through ridges on an upper face of the pad. Because each needle can only be attached to a ridge by puncturing the resilient material, each needle must be pointed or sharp and it must be proper oriented to puncture.

U.S. Pat. No. 5,590,774 to Roberts (hereinafter "Roberts") discloses a surgical needle discard container with a rotatably attached lid for inserting used surgical needles. However, proper use of the Roberts' container requires two hands to rotate the lid once a needle is inserted into the container. Even in a situation where the Roberts' container may be attached to another item such that only one hand is needed to rotate the lid, touching the lid with a hand during surgery may allow for contamination and/or needle stick injury in an attempt to move the lid of the container.

Among the above devices used to receive and store needles, there are additional shortcomings. For example, despite having consecutively numbered zones, some of the above devices may lead to confusion in the accounting of instruments. In such devices, needles or other surgical instruments may be positioned over a border and in multiple zones. In particular, an unoccupied zone may appear to be occupied when it actually is not. An inability to efficiently count surgical instruments is an inconvenience to the surgeon or scrub nurse performing the counting and it may lead to delays, and thus complications, as a result. In some devices, touching the actual device with one's hands) is required, thus potentially risking injury to the hands of the individual touching the device.

Thus, what is desired is a storage device that has an ergonomic construction and will allow a user to avoid injury, increase efficiency in counting and positioning different types of needles and other surgical devices, and significantly decrease inadvertent needle sticks to the medical staff by not requiring that hands of the medical staff need to touch the device.

SUMMARY OF THE INVENTION

Various exemplary embodiments of the present invention include a device for retaining medical sharps after surgical use. The device is comprised of a base, a tray, and a cover. The base has a bottom side, a topside, and a center post directed up and away from the topside of the base. The tray has multiple dividers separating individualized slots, and has a center opening through which the center post may be housed. The cover has a cover opening of a substantially similar size as that of one individualized slot of the tray, and has a top cover opening able to house the center opening of the tray and the center post of the base. A button is located on a topmost position of the center post which, when depressed, slightly deforms the base and causes the tray to advance about the center post in a space substantially equal to the space of an individualized slot.

Various exemplary embodiments of the present invention include a method of retaining used medical sharps of a medical procedure. The method is comprised of the steps of first using a medical sharp during a medical procedure. Next, the medical sharp is disposed of by placing the medical sharp into a slot of device. The device is comprised of a base, a tray, and a cover. The base has a bottom side, a topside, and a center post directed up and away from the topside of the base. The tray has multiple dividers separating individualized slots, and has a center opening through which the center post may be housed. The cover has a cover opening of a substantially similar size as that of one individualized slot of the tray, and has a top cover opening able to house the center opening of the tray and the center post of the base. Next, a button, located on a topmost position of the center post, is depressed to slightly deform the base and cause the tray to advance about the center post in a space substantially equal to the space of an individualized slot. Then the medical procedure proceeds and the aforementioned steps are repeated for each used medical sharp. Upon the close of the medical procedure, the device is examined to ensure all used medical sharps are accounted.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION OF THE PREFERRED EMBODIMENTS

Figure 1:
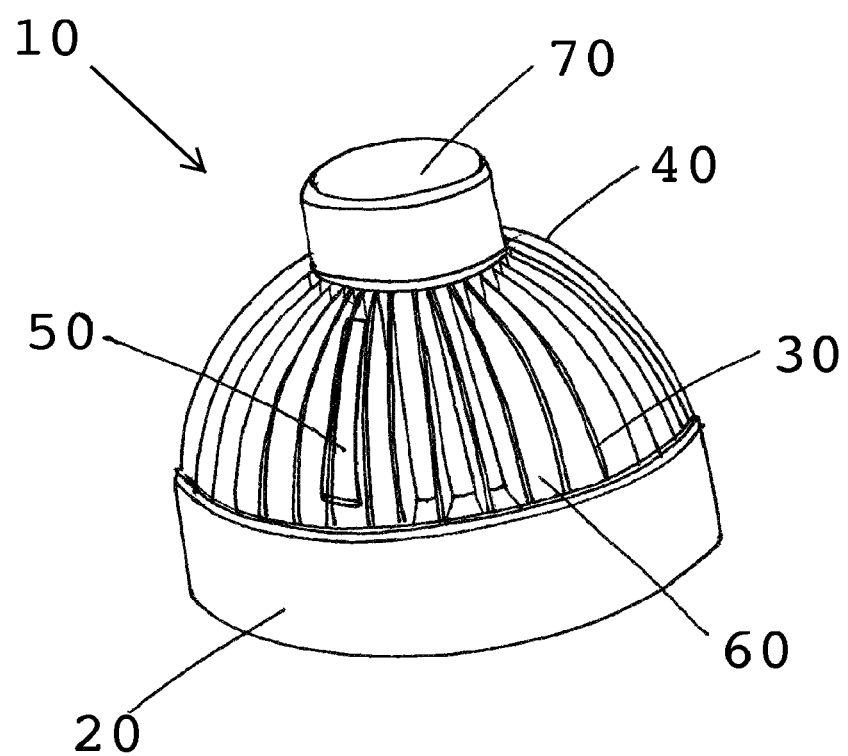
FIG. 1 is a perspective view of an exemplary embodiment of the present invention.
Figure 2:
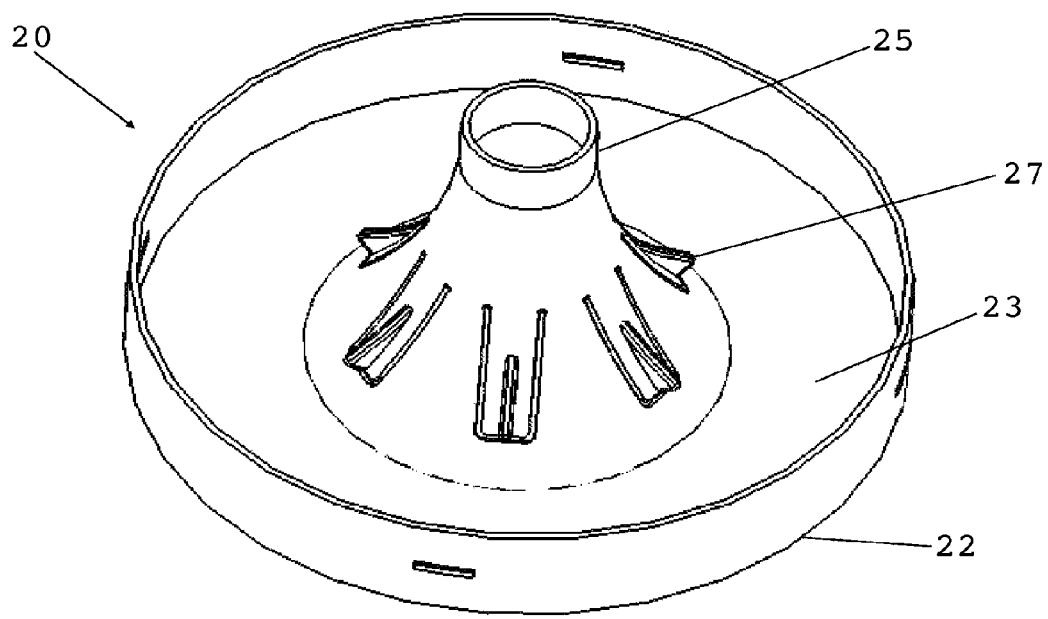
FIG. 2 is an illustration of the base of an exemplary embodiment of the present invention.
Figure 3:
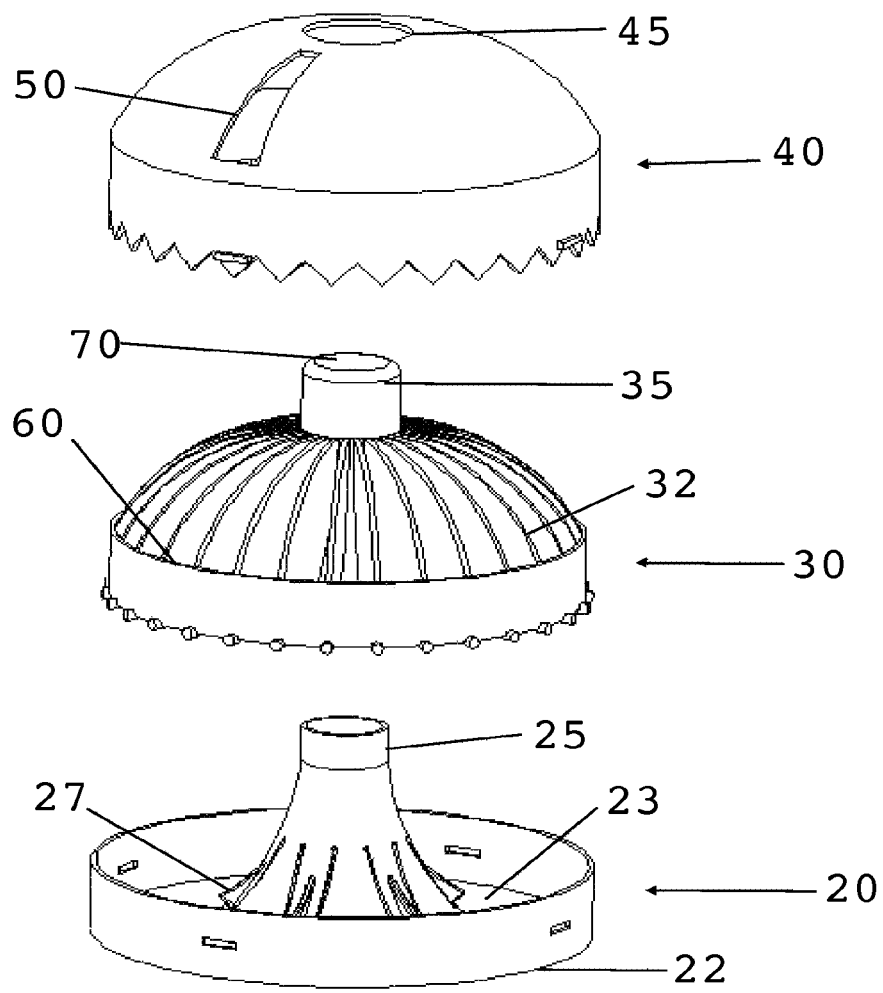
FIG. 3 is an illustration of the three primary parts, not attached to one another, of an exemplary embodiment of the present invention.

FIG. 1 illustrates a storage device 10 for medical sharps such as, for example, needles, scalpels, knives, etc. The storage device includes a tray 30 having multiple dividers, wherein a single slot 60 is located between two dividers. The storage device also has a base 20, and the tray is positioned on the base. A cover 40 is positioned substantially over the tray and has a cover opening 50 which reveals an exposed slot. In a preferred embodiment of the present invention, the base and the cover attach to each other.

The base has a bottom side 22 and a top side 23. The base preferably has a circular footprint and a may have a sidewall formed at the perimeter of the base.

A center post 25 rises upward and away from the topside of the base. A lower portion of the center post, in a preferred embodiment, has a conical shape, while an upper portion of the center post is more cylindrical in shape. Multiple fins 27 may be attached lengthwise to the center post.

The tray has multiple dividers which define individual slots. It is preferred that the multiple dividers 32 and multiple individual slots 60 all be substantially equal in shape and size, respectively.

The tray is preferably circular in shape such that it fits the footprint of the base.

The tray may include a fabric, sponge, or sponge-like material in a lower portion of each slot.

The tray includes a center hub 35 around which radiate the multiple individual slots and multiple dividers. The center hub is sized to house the center post of the base, such that the center post extends into the center hub.

The cover has a cover opening 50 of a substantially similar size as that of one individual slot of the tray. The cover is preferably connectable and/or attachable to the base such that the tray is positioned between the base and the cover.

The cover has a recess 45 which houses the center hub of the tray and the center post of the base. It is preferred that the cover be transparent such that one can discern the occupancy of each slot of the tray when the device is assembled.

A button 70 is located on or formed by a topmost position of the center post. When the button is depressed, the center post slightly deforms the base and causes the tray to advance about the center post in a space substantially equal to the space of an individual slot.

Figure 4:
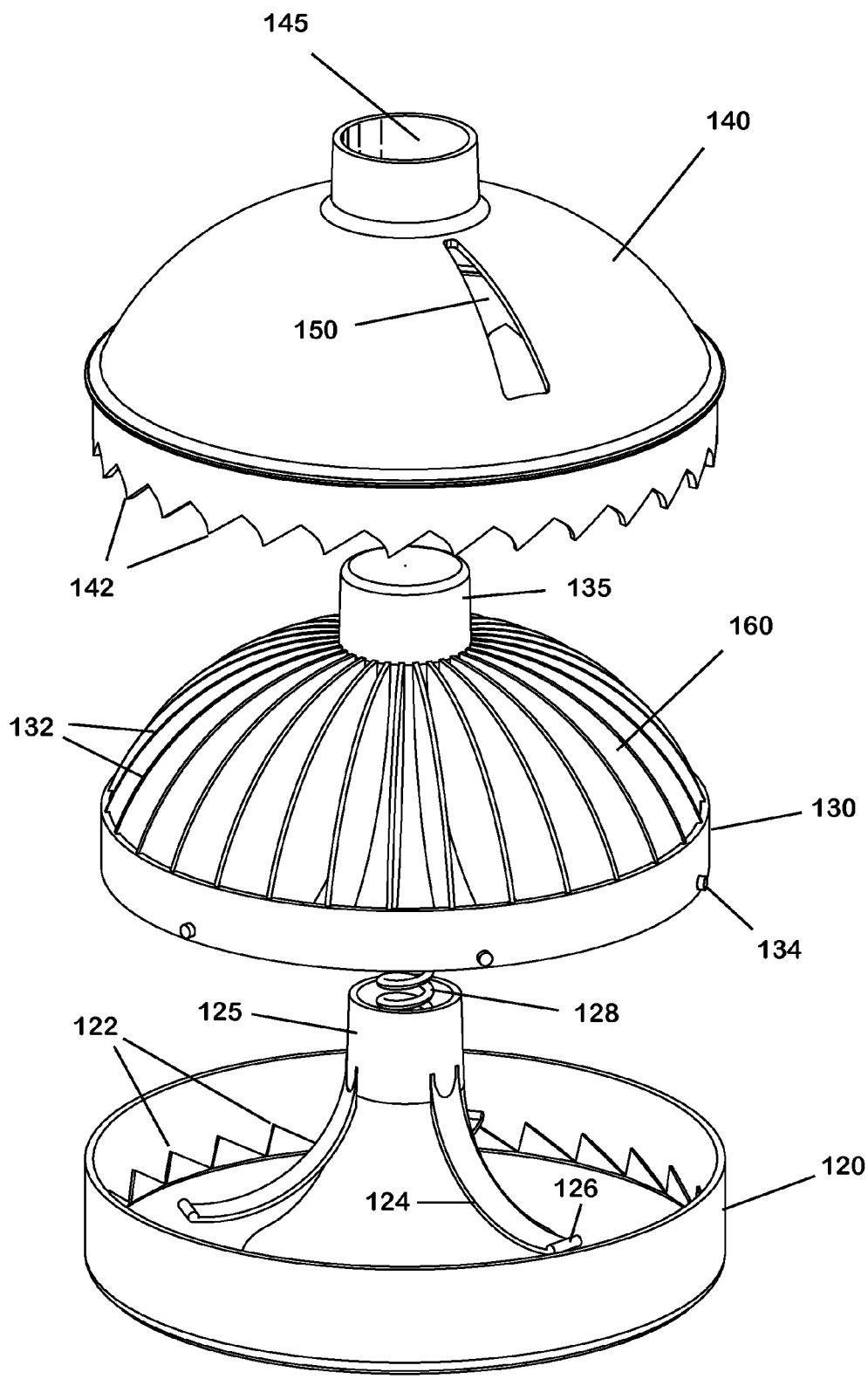
FIG. 4 is an exploded perspective view of a further embodiment of the invention.
Figure 5:
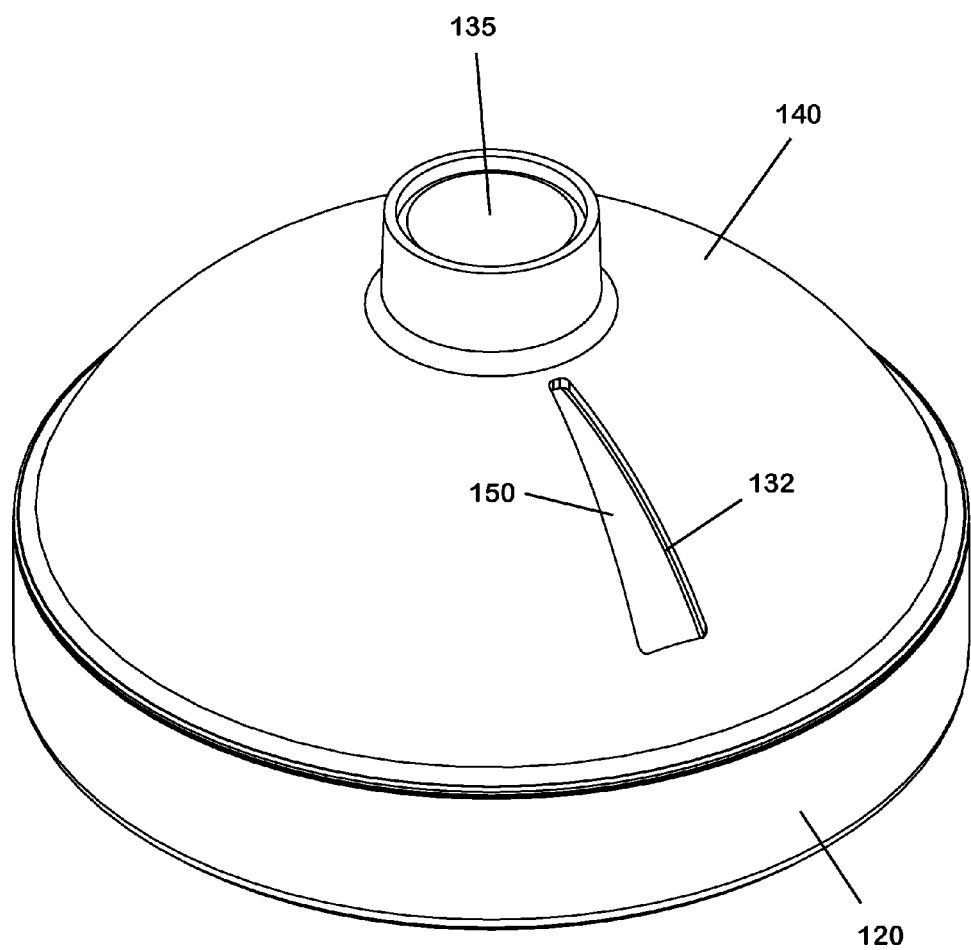
FIG. 5 is an unexploded perspective view of the embodiment of FIG. 4.

FIGS. 4 and 5 illustrate another embodiment of the invention. As shown in FIG. 4, the base 120 has a series of ratchet teeth 122 on the inner periphery of its rim, the angular spacing or pitch between the teeth being identical to the angular spacing between the dividers 132. For example, it there are thirty dividers, both the dividers and the ratchet teeth have a pitch of 12°. Each ratchet tooth has the shape of a triangle, the upper sides of which lie at different angles to promote unidirectional motion. For example, one side may make an angle of about 15° with the vertical (assuming the axis of the device is vertical), and the other may make an angle of about 60° with vertical.

Three leaf springs 124 are formed integrally with the base, extending outward from its center post 125. The tips 126 of the leaf springs press upward against the bottom of the tray, keeping the tray in its uppermost position normally. A coil spring 128, situated in a well in the center portion of the base, is also provided to bias the tray upwardly. It might be possible to modify the device by eliminating either the coil spring of the leaf spring; in any event at least one spring is necessary to bias the tray toward its uppermost position.

The cover 140 has teeth 142 formed on its bottom rim, these teeth having the same angular spacing as the ratchet teeth, e.g., 12°. When the cover is assembled on the base, a zigzag gap is exists between the ratchet teeth 122 and the cover teeth 142. Each of the cover teeth is asymmetrical, having one lower side substantially parallel to one side of an opposed ratchet tooth, and another lower side parallel to the other side of the ratchet tooth.

The tray 130, which is confined between the base 120 and the cover 140, has a plurality of (for example, six) projections 134 extending outward from its outer periphery into the zigzag gap. When the tray is pressed downward, the projections 134 engage the ratchet teeth, which advance the tray in one rotational direction (e.g., clockwise). When the tray is released, the tray is pressed upward by the springs, so that the projections engage the teeth on the cover and complete an increment of angular movement (12°, in the example given).

The tray has a center hub 135 whose flat top serves as a button which extends through the center hole in the cover. When the hub is depressed by a finger with sufficient force, the coil spring 128 between the tray and the base is compressed, and the leaf springs 124 in the base are deflected, allowing the tray to move downward to increment the position of the tray. When the button is released, the tray returns to its original position, bearing against the cover.

In use, a medical sharp, needle, or other surgical instrument is inserted through the cover opening into the exposed slot. Then the tray is rotated to a next position by depressing the button, so that an immediately adjacent slot becomes the exposed slot. Once an occupied slot is rotated away from the opening in the cover, it is substantially inaccessible, and its contents are prevented from intermixing with contents of other slots.

One may monitor the slots to account for all needles and/or other surgical instruments used in an operation. To facilitate monitoring the cover may be made of a substantially transparent material. Preferably, cover is a medical grade plastic that substantially prevents puncturing by a medical sharp, needle, or other surgical instrument.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. A device for retaining medical sharps after surgical use, said device comprising:
    a base having a floor and a center post extending upward from said floor;
    a tray having multiple dividers defining individual slots, and having a center hub which houses the center post; and
    a cover having a cover opening of a substantially similar size as one of the slots of the tray, and having a central opening housing the center hub of the tray;
    said cover and said base confining the tray but permitting limited movement of the tray between an upper position and a lower position; and
    at least one spring biasing said tray toward said upper position,
    wherein the center hub serves as a button which can be depressed to push the tray to said lower position, and further comprising
    a mechanism which causes the tray to advance about the center post in an angular increment equal to the space of an individualized slot each time the button is depressed.

2. The device according to claim 1, wherein the cover has an annular skirt extending from a bottom surface thereof and said mechanism comprises
    a first circumferential array of teeth formed in the base,
    a plurality of projections extending from the tray in positions to engage said first plurality of teeth when the tray is in said lower position, and
    a second circumferential array of teeth formed on the a skirt, said projections also being in positions to engage the second plurality of teeth when the tray is in said upper position, each of said teeth being asymmetrical so as to produce unidirectional angular movement of the tray.

3. The device according to claim 1, wherein the at least one spring comprises a coil compression spring situated between the base and the cover.

4. The device according to claim 1, wherein the at least one spring comprises at least one leaf spring formed integrally with the base and pressing upward on a bottom surface of the tray.

5. The device according to claim 1, wherein uppermost edges of the multiple dividers are substantially adjacent to the cover when the device is assembled.

6. The device according to claim 1, wherein the cover is substantially transparent.

* * * * *